United States Patent [19]

Bauer

[11] Patent Number: 4,658,810

[45] Date of Patent: Apr. 21, 1987

[54] METHOD OF CONTRACEPTION AND A DEVICE THEREFOR

[76] Inventor: Hans A. Bauer, Südliche Stadtmauer-strasse 58, Erlangen 8520, Fed. Rep. of Germany

[21] Appl. No.: 726,911

[22] Filed: Apr. 23, 1985

Related U.S. Application Data

[63] Continuation of Ser. No. 514,640, Jul. 18, 1983, abandoned.

[30] Foreign Application Priority Data

Jul. 31, 1982 [DE] Fed. Rep. of Germany ....... 3228704

[51] Int. Cl.[4] .............................................. A61F 5/46
[52] U.S. Cl. ................................................... 128/130
[58] Field of Search .................... 604/55; 128/128–131

[56] References Cited

U.S. PATENT DOCUMENTS 3,820,535 6/1974 Marco ................................ 128/130

FOREIGN PATENT DOCUMENTS 1430532 3/1976 United Kingdom .................. 604/55

Primary Examiner—John D. Yasko
Attorney, Agent, or Firm—Holman & Stern

[57] ABSTRACT

The present invention discloses a method of contraception employing an intrauterine device comprising retaining means for retaining a contraception element within a uterine cavity. The retaining means includes anchoring means for penetrating into and positively engaging the uterine muscle, so that the device is securely retained in the cavity. The device also preferably includes associated driving means for driving the anchoring means into the uterine muscle. A new device for contraception is also disclosed.

11 Claims, 7 Drawing Figures

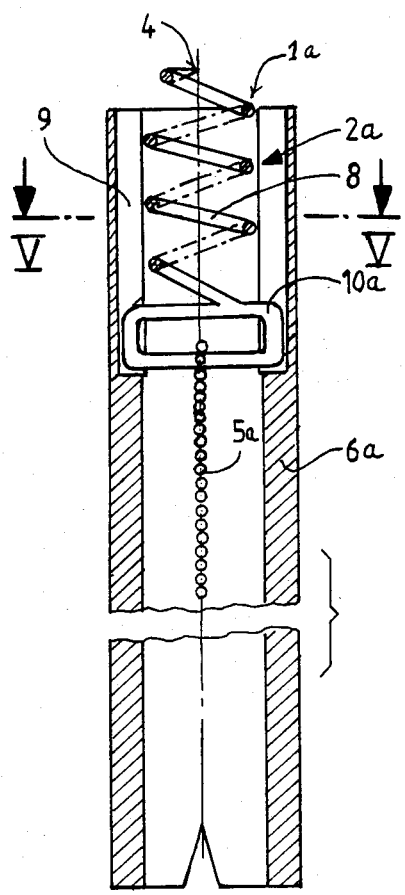
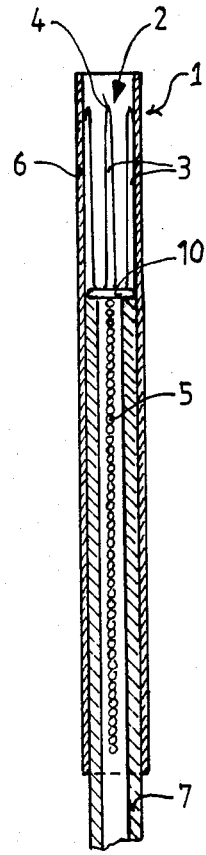
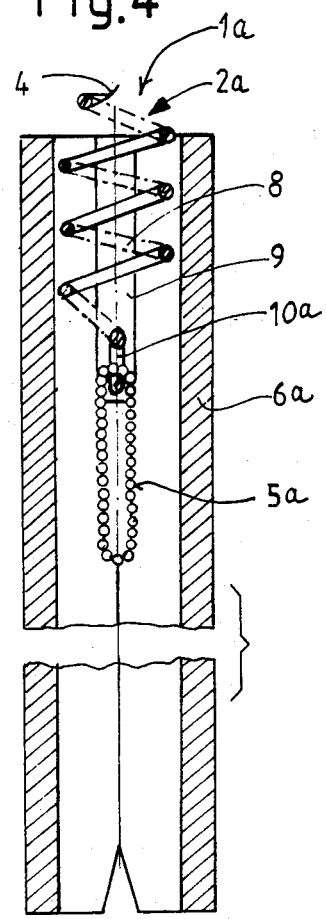
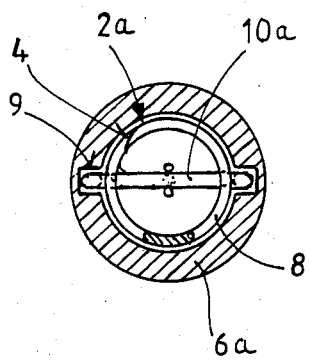
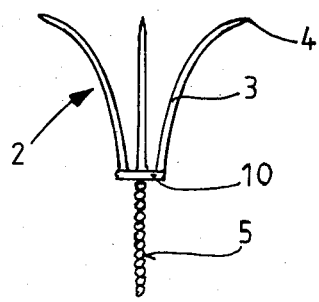
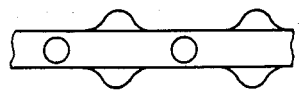

METHOD OF CONTRACEPTION AND A DEVICE THEREFOR

This is a continuation of application Ser. No. 514,640, filed July 18, 1983, now abandoned.

BACKGROUND OF THE INVENTION

Intrauterine devices known to the prior art are typically secured within the uterine cavity by conforming the device to the contours of the cavity. Since the uterine cavity increases in cross-section in the direction of the fundus, conventional means for retaining the device within the cavity are adapted to this conformation. For example, devices in common use include T-shaped devices, wherein the sidearms of the "T" extend into the wider section of the cavity, thereby retaining the device within the uterus. Notwithstanding the shape-adapting conformation of such devices, they are frequently involuntarily expelled, owing to especially strong contractions of the musculature of the uterus, failure of the device to conform adequately to the conformations of individual uterine cavities, or for other reasons.

It is accordingly an object of the invention to provide a method of contraception comprising employing an intrauterine device (IUD) which is reliably retained within the uterine cavity, and which is not dependent for retention upon a precise conformation.

SUMMARY OF THE INVENTION

The invention comprises an intrauterine device including retaining means for penetrating into and engaging the uterine muscle wall and for retaining the device within the uterine cavity. Preferably, the IUD includes contraception means comprising a source of metallicions, especially iron, copper, silver, gold or platinum, which are slowly released into the uterine cavity and promote contraception. The IUD of the invention further includes, associated driving means for driving the retaining means into penetrating engagement with the muscle wall; the driving means is disassociated from the IUD and withdrawn after the device has been secured.

BRIEF DESCRIPTION OF THE DRAWINGS

FIG. 1 is a side view of an IUD retaining means according to the invention;

FIG. 2 is a cross-sectional view of one embodiment of an IUD of the invention, with associated driving means;

FIG. 3 is a cross-sectional view of an alternate embodiment of an IUD according to the invention, also including associated driving means;

FIG. 4 is a cross-sectional view of the IUD of FIG. 3, rotated 90°; and

FIG. 5 is a cross-sectional view of the IUD of FIG. 3 along the line V—V.

FIGS. 6(a) and 6(b) show fragmentary view of protuberances and depressions on the helix.

DETAILED DESCRIPTION OF THE INVENTION

The underlying concept of the invention is the retention of an IUD by retaining means which penetrate into and engage the uterine muscle wall so that the IUD is retained within the cavity against forces which tend to its expulsion. Retaining means of the type generally employed for anchoring pacemakers within the cardiac muscle are suitable. Retaining means having spring biased anchoring elements which embed themselves into the muscle after penetration are exemplary. Suitable retaining means of this type include those incorporating one or more arcuate, elongated, wire-like anchoring elements, such as the weakly curved hooks of spring wire illustrated in FIG. 1. Such retaining means are easy to insert, and are also easy to remove. It is further advantageous if the anchoring element includes a point on its free end, which facilitates insertion into the muscle. Two or more barbed anchoring elements may be provided in conjunction with a central anchoring element; the barbed elements are retained against the central element during insertion, and are released to positively engage the muscle structure after insertion. IUDs of this type may be removed in the same manner as are similar structures on cardiac pacemakers. Alternate retaining means include those of the type incorporating a helical anchoring element which may be screwed into the muscle wall. These are particularly easy to insert and withdraw, and to reset if the tip is inadvertently set too deeply or the muscle wall is penetrated. It is most important that the retaining means *just* penetrate into the muscle sufficiently to permit it to embed therein; complete penetration through the muscle wall is to be avoided.

Suitable driving means comprise means adapted to cause the anchoring elements of the particular IUD to penetrate the muscle wall, and which are further adapted for manipulation within the uterine cavity. Exemplary driving means include hollow tubes operatively associated with the retaining means to cause rotation or plunging thereof so that the anchoring elements of the IUD are inserted into the musculature. Preferably, the retaining means includes stop means associated with the anchoring elements to prevent these elements from being inserted too far into the muscle. Various stop means are suitable, such as the transverse element exemplified.

The IUD of the invention further includes contraception means retained in the uterine cavity by the IUD retaining means. In the embodiments illustrated, the contraception means comprises an ion-releasing contraception element, which is advantageously elongated and may be, e.g., in the form of a wire helix, the coils of which lie closely together. If an elongated element is provided which runs coaxially with the anchor, it is particularly easy to bring this element along with the retaining means through the cervical channel. Also, such an elongated element can be readily accommodated in an instrument used to insert the device into the muscle. The contraception means may also be in the form of a chain, with beaded or other links. Since the chain will follow the force of gravity as the bodily position changes, the surface of the chain will be continually automatically cleaned as it rubs against and slides over the mucous membrane. This automatic cleaning permits the IUD to have a longer residence time than is possible with known IUDs, and provides a uniform rate of release of ions.

It is particularly advantageous for the intrauterine device to be entirely metallic. This avoids introducing any kind of plastic into the uterine cavity In this way, there is no conversion of nonpathogenic microorganisms to pathogenic status of form, and no development of reactions of the type which occur with porous plastic. Preferably, both the retaining means and the ion-releasing contraception means are comprised of steel, copper, silver, gold, platinum or other pharmaceutically acceptable metals. The driving means for inserting the IUD is suitably of plastic.

The inventive IUD includes the following advantages: After precise insertion there is no risk of spontaneous expulsion. Mismatching between the cavum uteri and the IUD is not a factor. Hemorrhaging due to mechanical injury to mucous membranes is avoided. With a full bladder, the muscular strength of the fundus and the positioning of the IUD can be monitored by means of ultrasound. The IUD is completely visible in X-ray photographs. The complication rate is very low, regardless of the configuration of the uterine muscle and the cavum. The IUD reacts purely passively to active movement of the uterus musculature. Because the inventive IUD remains securely in place, a checking thread may be dispensed with; thus, infections caused by such threads are eliminated.

In a specific embodiment of the invention, a metallic contraception element may be fastened to one end of a plastic filament piece disposed in a hollow needle capable of pressing or injecting the free end of the filament, which is softened, into the muscle. A small amount of plastic material is thus forced into the muscle; this plastic material hardens and forms a small ball on the embedded end of the filament. After the hollow needle is withdrawn, the filament with the attached contraception element part remains fixed in the uterine muscle. The IUD can be withdrawn from the muscle without noticeable damage by pulling on the filament, since the ball configuration can exit through the channel formed by the filament; in so exiting the ball anchoring element does not cause damage, due to the elasticity of the muscle tissue.

With particular reference to the Drawing, FIGS. 1 and 2 illustrate an IUD according to the invention generally indicated at 1. The IUD 1 includes retaining means generally indicated at 2 including anchoring elements comprising four spring arms 3 attached to stop means comprising transverse disc-shaped element 10. Each spring arm 3 has a free end bent or curved outwardly, and coming to a point 4. Each of the arms 3 is of a metal material. Contraception means comprising a straight copper beaded chain 5 is attached to the retaining means 2 via transverse element 10. The IUD 1 is associated with driving means comprising a hollow tube 6, in which the arms 3 are retained in a straight configuration. A hollow piston 7 is disposed within the tube 6 for axial movement therewithin; the piston 7 accommodates the chain 5 and presses against the transverse element 10 from below. The anchoring elements comprising spring arms 3 are inserted into the muscle wall by placing the forward end of the tube 6 against the muscle and pushing against the piston 7; the IUD is thus driven forward and the spring arms 3 penetrate into the muscle and spread outwardly to positively engage the muscle and embed the IUD in the muscle wall, until stop means 10 contacts the muscle.

With reference to FIGS. 3, 4 and 5, the IUD 1a includes retaining means 2a with an anchoring element comprising a helical coil 8 comprised of a metal material and terminating in a point 4. The retaining means 2a further includes stop means comprising a beam-shaped transverse element 10a, and contraception means comprising an elongated looped chain 5a. (The chains 5 and 5a in actual use will be longer, proportionally, than illustrated; a useful length would be about 10× the illustrated length in proportion to the other elements of the IUDs 1 or 1a.)

The IUD 1a is associated with driving means comprising a hollow tube 6a having two slots 9 on the forward end thereof for engaging the transverse element 10a as best shown in FIG. 5. The tube 6a functions to guide the IUD 1a through the vagina to the uterine muscle, and to embed the anchoring element or helical coil 8. The transverse element 10a is axially displaceable within the forward portion of the tube 6a, and as the tube 6a is rotated, the point 4 of helical coil 8 engages and penetrates the muscle wall. By rotation of the tube, the helical coil 8 is simultaneously withdrawn from the tube 6a and is further embedded, until the stop means or transverse element 10a contacts the muscle tissue. At this point, the tube 6a is withdrawn from the body. The helical coil 8 is preferably an elongated wire-like, backward catching piece, which has a plurality of depressions or protuberances as shown in FIGS. 6(a) and 6(b) disposed on the surface thereof to inhibit unintended withdrawal from the muscle by reverse rotation of the helix.

What is claimed is:

1. A method of contraception comprising employing an intrauterine device having an elongated metal chain-like means for producing ions in a utering cavity and anchoring said device in the cavity by an anchoring element disposed about said elongated means, said elongated means being substantially coaxial with the anchoring element, said anchoring element being a helix provided with point means for anchoring said device at the base of uterine musculature by rotating the helix in a screw-like fashion.

2. The method of claim 1, wherein the anchoring element comprises one or more arcuate, elongated wire-like anchoring elements.

3. The method of claim 1, further including associated driving means for driving the anchoring element into penetrating engagement with the uterine muscle.

4. The method of claim 1 wherein a cross piece is provided at a distance from said point means.

5. The method of claim 1 wherein the helix is provided with depressions or elevations.

6. The method of claim 1 wherein said device is insertable into an elongated tube and provided with means for ejecting the device into said cavity wherein the intrauterine device together with the helix is located within the tube and provided with a cross piece which engages in a slot in the tube.

7. The method of claim 1 wherein said elongated means changes position by gravity in response to positional change in uterine cavity, rubbing against and sliding over the mucous membrane of the uterine musculature.

8. The method of claim 1 wherein said elongated means is free of plastics material.

9. An intrauterine device comprising contraception means having an elongated metal chain-like means for producing ions in a uterine cavity for preventing conception and retaining means for retaining the contraception means within a uterine cavity, said retaining means including a helical coil anchoring means for penetrting into and positively engaging the uterine muscle by rotation of the helical coil anchoring means in a screw-like fashion so that the contraception means is retained within the uterine cavity.

10. The invention of claim 9, wherein said driving means comprises a hollow tube engageable with said retaining means for rotation therewith and associated driving means for driving the anchoring means into penetrating engagement with the uterine muscle.

11. The invention of claim 9, further including stop means for stopping the movement of the anchoring elements into the muscle wall.

* * * * *